United States Patent [19]

Park

[11] Patent Number: 4,880,835

[45] Date of Patent: Nov. 14, 1989

[54] ORAL LIQUID PHARMACEUTICAL COMPOSITIONS OF SULINDAC

[75] Inventor: Moo K. Park, Rockville, Md.

[73] Assignee: Formulations Development Labs, Inc., Wilmington, N.C.

[21] Appl. No.: 266,660

[22] Filed: Nov. 3, 1988

[51] Int. Cl.$^4$ .............................................. A61K 31/19
[52] U.S. Cl. .................................................... 514/570
[58] Field of Search ................................. 514/569, 570

[56] References Cited

U.S. PATENT DOCUMENTS 3,654,349 4/1972 Sten et al. ....................... 260/515 M
4,307,114 12/1982 Dvornik et al. .................... 514/569

OTHER PUBLICATIONS

Physicians Desk Ref., p. 1251 (1986).
Merck Index, p. 1290, 10th Ed., 1983.

*Primary Examiner*—Stanley J. Friedman
*Attorney, Agent, or Firm*—William H. Edgerton

[57] ABSTRACT

Pharmaceutically elegant oral liquid compositions of sulindac are prepared using calcium sulindac in a vehicle comprising a glycol, a polyol, optional ethanol and pharmaceutical additives.

8 Claims, No Drawings

ORAL LIQUID PHARMACEUTICAL COMPOSITIONS OF SULINDAC

This invention relates to one phase, liquid compositions containing sulindac for oral administration to human subjects in need of anti-inflammatory treatment.

BACKGROUND OF THE INVENTION

Sulindac, chemically cis-5-fluoro-2-methyl-1-[(p-methylsulfenyl)benzylidene [indene-3-acetic acid, is a non-steroidal anti-inflammatory agent which is marketed only in 150 gm. and 200 mg. tablets for oral administration 1-3 times daily (Physician's Desk Reference 1987, p.1251). The parent acid is very insoluble in water and especially in methyl or ethyl alcohol (Merck Index 10th Edition, 1983, p.1290). The compound is erratically absorbed from the gastrointestinal tract. Oral liquids of sulindac have not been easily available to the medical art because of the bitter taste of the drug. U.S. Patent Number 3,654,349 discloses a number of pharmaceutical forms of sulindac, column 4, lines 3-25. The sodium and calcium salts are described in Examples 16 and 17 of the patent as being prepared by the reaction of the parent acid with the respective alkali metal methoxide in methanol.

There is a need in the pharmaceutical art for an elegant, oral liquid composition of sulindac for treating patients who have difficulty ingesting solid compositions such as tablets or capsules.

SUMMARY OF THE INVENTION

This invention relates to one phase, liquid pharmaceutical compositions of sulindac which are useful for oral administration to patients in need of anti-inflammatory treatment. The compositions contain a therapeutic quantity of calcium sulindac dissolved in a mixture of pharmaceutically acceptable glycols and polyols.

DETAILED DESCRIPTION OF THE INVENTION

This invention is based on the favorable physical characteristics of a selected alkali metal salt of sulindac. The calcium salt has good stability, can be used for preparing oral compositions per se or in situ and has unexpected solubility in certain pharmaceutically acceptable glycols such as propylene glycol, polyethylene glycols or poly-propylene glycols. The pH of solutions of calcium sulindac is acceptable for formulation compared with that of sodium sulindac solutions. The latter salt also is strongly hygroscopic and difficult to crystallize in our hands in contrast with the useful properties of the calcium salt.

The oral liquid compositions of this invention comprise from 0.5-7%, preferably 1-5%, w/v of calcium sulindac; 15-50%, preferably from 20-40%, v/v of a glycol such as polyethylene glycol or propylene glycol; from 0-20%, v/v of ethanol; and from 30-80%, preferably 35-75%, v/v of a polyol such as sorbitol or glycerin. Other pharmaceutical additives may be added such as sweetening agents, for example, saccharin calcium, sucrose or artificial sweetening agents, local anesthetics, anti-bacterials and the like. The oral composition are clear liquids of good stability, usually yellow-orange in color. The liquid preparations of this invention are usually prepared to deliver from about 100-250 mg of drug per teaspoon in a pleasant tasting, elegant pharmaceutical composition in easily bioavailable form with minimal irritability of the gut.

This invention also comprises the method of anti-inflammatory treatment of human subjects in need thereof such as those having osteoarthritis, rheumatoid arthritis, bursitis or gouty arthritis by the administration thereto orally of the pharmaceutical compositions described above in non-toxic, effective quantities.

The glycol and polyol constituents of this invention are those acceptable for internal pharmaceutical purposes. The glycol may be propylene glycol or one of the polyalkylene glycol products such as those known in the art as the "PEG" series with chemical structures having 2 or 3 carbon atoms in the alkylene moiety and a mean molecular weight of 200 to 4000. The polyol constituent comprises pharmaceutically acceptable solvent compounds having more than two hydroxyls such as glycerin or sorbitol.

The compositions of this invention are prepared by mixing the constituents, filtering the mix and filling into bottles of appropriate size.

The calcium sulindac is prepared by reacting sulindac with a stoichiometric quantity of calcium hydroxide in aqueous ethanol at room temperature. The mixture clears and the desired calcium salt then separates from the reaction mixture.

The following examples are designed to teach the practice of this invention but not to limit the scope of invention.

EXAMPLE 1

100 g Sulindac is suspended in 4 l. of 75% v/v ethanol. Apply heat until a clear solution is formed. Add 10.38 g of calcium hydroxide and mix. A clear solution is formed initially followed by massive precipitation of calcium sulindac. Filter the slurry to remove the solvent and air dry to give calcium sulindac.

EXAMPLE 2

Preparation of Oral Liquid of Calcium Sulindac Using the Salt of Example 1.

|  | #1 | #2 |
| --- | --- | --- |
| Calcium Sulindac | 4.4 g | 4.4 g |
| Ethanol 100% USP | 10 ml | 20 ml |
| Propylene Glycol USP | 25 ml | 25 ml |
| Ca Saccharin | 0.3 g | 0.3 g |
| Menthol | 0.2 g | 0.2 g |
| Eucalyptus Oil | 0.1 ml | 0.1 ml |
| Glycerin q.s. ad | 100 ml | 100 ml |

Manufacturing Directions:
1. Dissolve calcium saccharin, menthol and eucalyptus oil in ethanol.
2. Add propylene glycol to #1 and mix.
3. Add calcium sulindac to #2 and mix.
4. Add glycerin and mix until a clear solution is obtained.
5. Filter through clarifying filter and fill the filtrate into bottles.

The clear liquid from above is administered orally to a subject in need thereof in quantities of one teaspoon (200mg) from 1-3 times daily.

EXAMPLE 3

Preparation of Sulindac Oral Liquid By In-Situ Salt Formation.

|  | #3 | #4 |
| --- | --- | --- |
| Sulindac | 4 g | 4 g |
| Ethanol 100% | 10 ml | 10 ml |
| Water | 5 ml | 5 ml |
| Calcium Hydroxide | 0.415 g | 0.415 g |
| Menthol | 0.2 g | 0.2 g |
| Calcium Saccharin | 0.3 g | 0.3 g |
| Propylene Glycol | 25 ml | 25 ml |
| Sorbitol Solution, 70% q.s. ad | 100 ml | — |
| Glcerin q.s. ad | — | 100 ml |

Manufacturing Directions:

1. Mix ethanol, water and propylene glycol in a container.
2. Add sulindac, calcium hydroxide and calcium saccharin and mix with gently heating until all the particles dissolve.
3. Add menthol and dissolve.
4. Add sorbitol solution or glycerin to make up the volume.
5. Filter through clarifying filter and fill.

EXAMPLE 4

A. Solubility of sulindac and its calcium salt.

Solubility data are summarized in Table I as shown below. The calcium salt shows a big increase in solubility over its free acid form in all the solvents studied which was unexpected. Propylene glycol is an excellent solvent for calcium sulindac.

TABLE I

| Solubility of Sulindac and Calcium Sulindac at 25 C, w/w% | | | |
| --- | --- | --- | --- |
| Solvent | Sulindac | Ca Sulindac | Na Sulindac |
| Propylene Glycol | 0.71 | 33.4 | — |
| PEG 400 | 3.55 | 17.6 | — |
| Glycerin | 3.52 | 13.7 | — |
| Water | — | — | 15. |

B. Oral liquids of calcium sulindac #1–#4, from Examples 2 and 3 above which are prepared using Ca salt or in situ Ca salt formation are all clear solutions. The organoleptic characteristics of the solutions are acceptable with a pleasant taste for oral administration. pH Measurement is made on samples of Formulas #3 and #4 diluted with water at 1:10 ratio on a volume basis. The results are shown below.

TABLE II

| pH Of 1:10 Diluted Calcium Sulindac Oral Solutions at 25 C. | | |
| --- | --- | --- |
| Formulas | pH | Appearance of diluted solution |
| #3 | 6.13 | Clear solution no precipitate. |
| #4 | 6.02 | Slightly turbid no precipitate. |

In contrast, an aqueous solution of 4% sodium sulindac shows pH of 10.99.

What is claimed is:

1. A one phase liquid composition for oral administration comprising:
    (a) An anti-inflammatory but non-toxic quantity of calcium sulindac selected from the range of 0.5–7% w/v;
    (b) a pharmaceutically acceptable quantity of a glycol which is propylene glycol or a polyethylene glycol selected from the range of 15–50% v/v;
    (c) a quantity of ethanol selected from the range of 0–20% v/v; and
    (d) a pharmaceutically acceptable quantity of a polyol which is glycerin or sorbitol selected from the range of 30–80% v/v.
2. The composition of claim 1 in which the glycol is propylene glycol and the quantity is selected from 20–40% v/v.
3. The composition of claim 1 in which the polyol is glycerin and the quantity is selected from 35–75% v/v.
4. The composition of claim 1 in which the glycol is polyethylene glycol 400 and the quantity is selected from 20–40% v/v.
5. The composition of claim 1 in which the quantity of calcium sulindac is selected to give from 100–250 mg of sulindac per teaspoon.
6. The composition of claim 1 in which the glycol is polyethylene 400, the polyol is sorbitol and the calcium sulindac is generated in situ in a quantity selected from 1–5 w/v.
7. The composition of claim 1 in which the quantity of calcium sulindac is 4.4 g per 100 ml, the quantity of ethanol is from 10–20 ml per 100 ml, the quantity of propylene glycol is 25 ml per 100 ml, and the quantity of glycerin is used to make the solution up to 100 ml.
8. The method of inducing anti-inflammatory activity in a human subject in need thereof comprising administering orally to said subject a composition of claim 7 in a non-toxic, effective therefor quantity.

* * * * *